(12) United States Patent
Schiødt

(10) Patent No.: US 6,515,148 B2
(45) Date of Patent: Feb. 4, 2003

(54) PROCESS AND CATALYST FOR THE PRODUCTION OF γ-BUTYROLACTONES

(75) Inventor: Niels Christian Schiødt, Brønshøj (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 09/880,247

(22) Filed: Jun. 13, 2001

(65) Prior Publication Data

US 2002/0013479 A1 Jan. 31, 2002

Related U.S. Application Data

(60) Provisional application No. 60/212,644, filed on Jun. 19, 2000.

(51) Int. Cl.$^7$ .............................................. C07D 307/56
(52) U.S. Cl. ........................................................ 549/326
(58) Field of Search .................................. 549/295, 326

(56) References Cited

U.S. PATENT DOCUMENTS

| 4,175,089 A | 11/1979 | Heiba et al. |
| 4,285,868 A | 8/1981 | Heiba et al. |

FOREIGN PATENT DOCUMENTS

| GB | 1293556 | 10/1972 |

OTHER PUBLICATIONS

E. J. Corey, et al., "Carbolactonization of Olefins Under Mild Conditions By Cyanoacetic and Malonic Acids Promoted By Manganese (III) Acetate", *Tetrahedron*, vol. 26, No. 36, 1985, pp. 4291–94, Elsevier Science Publishers, Amderstam, NL.

William E. Fristad, et al., "Manganese (III) γ–Lactone Annulation with Substituted Acids", *Journal of Organic Chemistry*, vol. 50, No. 17, 1985, pp. 3143–3148, American Chemical Society, Easton, US.

*Primary Examiner*—Amelia Owens
(74) *Attorney, Agent, or Firm*—Dickstein Shapiro Morin & Oshinsky LLP

(57) ABSTRACT

Process for the catalytic preparation of γ-butyrolactone having the general formula

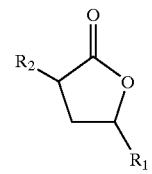

by reacting an olefin with the general formula $R_1CHCH_2$, with a carboxylic acid with a general formula $R_2CH_2COOH$, wherein $R_1$ and $R_2$ represent the substituent R1 and R2 in the butyrolactone, which reaction is performed in the presence of oxygen in contact with a catalyst comprising manganese and at least one basic metal oxide.

7 Claims, No Drawings

PROCESS AND CATALYST FOR THE PRODUCTION OF γ-BUTYROLACTONES

The present invention deals with the formation of γ-butyrolactone and substituted γ-butyrolactones of the general formula

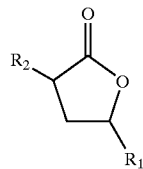

where $R_1$ and $R_2$ may be hydrogen, alkyl, cycloalkyl and aryl and may further contain functionalities such as ether and ester groups.

The invention is characterised by contacting an olefin of the general formula $R_1CHCH_2$, a carboxylic acid of the general formula $R_2CH_2COOH$ and oxygen in the vapour phase with a catalyst. The reaction which runs according to the following equation

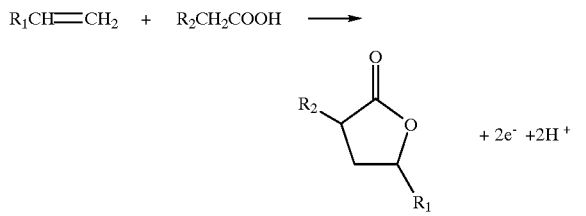

is carried out at a temperature of between 120° C. and 320° C. With oxygen as the electron acceptor (stoichiometric oxidant) water is formed as a by-product. The process may be carried out in continuous mode with the feed gas consisting of olefin, carboxylic acid, oxygen and optionally a diluent or it may be carried out in a recycling mode, where the catalyst acts as oxygen carrier.

The process may be carried out in a fixed-bed reactor, a fluid-bed reactor, a Riser reactor and other reactors, which may prove practical.

The catalyst is characterised by containing manganese and basic metal oxides (alkali, alkaline earth, rare earth and other basic oxides). The catalyst may be prepared by impregnation on a suitable support material and by precipitation of manganese salts together with other components.

The following example serves to demonstrate the concept and scope of the reaction.

A mixture of 1-octene and acetic acid was evaporated in a stream of nitrogen through a fixed bed of catalyst placed in a glass reactor mounted in a tubular oven. Experiments were carried out at 250–350° C. and normal pressure. The catalyst was an alumina supported, alkali promoted manganese catalyst. The effluent gas was passed through a condenser and the condensate was collected and analysed. The catalytic formation of n-hexyl γ-butyrolactone ($R_1=C_6H_{13}$, $R_2=H$) according to the equation

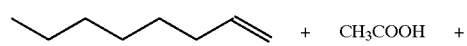 + CH₃COOH +

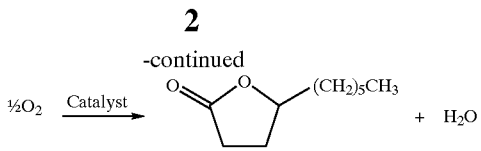 + H₂O was demonstrated by: (a) continuous formation of product (detected by GC/GC-MS) within a limited period of time; (b) ceasing product formation after this period and (c) renewed product formation after regeneration of the catalyst with air at 300–350° C.

EXAMPLES

The following Examples 1–5 concern the preparation of catalysts. The Examples 6 and 7 serve to illustrate the application of these catalysts in the process of this invention. In the case of impregnated catalysts, the support was crushed and sieved before impregnation. In all cases, the fraction 0.60–1.00 mm was used.

Example 1

Preparation of catalyst 1.

A high surface area alumina (5.11 g) was impregnated by the incipient wetness technique with a solution of NaOH (0.15 g) in water (5.0 ml). This product was dried overnight at 100° C. This intermediate product was impregnated with 5.0 ml of a saturated aqueous solution of Mn (II) acetate, and the product was calcined at 300° C.

Example 2

Preparation of catalyst 2.

A high surface area alumina (5.11 g) was impregnated by the incipient wetness technique with a solution of KOH (0.15 g) in water (5.0 ml). This product was dried overnight at 100° C. This intermediate product was impregnated with 4.0 ml of a saturated aqueous solution of Mn (II) acetate, and the product was calcined at 300° C.

Example 3

Preparation of catalyst 3.

A high surface area alumina (5.58 g) was impregnated by the incipient wetness technique with a solution of KOH (0.30 g) in water (5.0 ml). This product was dried overnight at 100° C. This intermediate product was impregnated with 4.5 ml of a saturated aqueous solution of Mn (II) acetate, and the product was calcined at 300° C.

Example 4

Preparation of catalyst 4.

This catalyst was prepared exactly as catalyst 1 except that the support was chromatography grade silica instead of alumina.

Example 5

Preparation of catalyst 5.

This catalyst was prepared by precipitation as follows. A solution of Mn $(NO_3)_2 \cdot 4H_2O$ (20.8 g) in 100 ml of water was slowly admixed with a solution of KOH (11.2 g) in 100 ml of water in a well stirred beaker. The slurry was continuously stirred and heated to 80° C. for one hour. The product was filtered off, washed with 1 liter of hot water and dried at 110° C. overnight. This material was calcined in air at 650° C. for 4 hours. The material was analysed by XRD and found to be pure $Mn_2O_3$.

The following example serves to demonstrate the catalytic nature of the reaction.

Example 6

Test of catalysts 1–3.

A 1:1 mixture of 1-octene and acetic acid was evaporated in a stream of nitrogen with a flow of 5 ml per hour through a fixed bed of catalyst (3 g) placed in a glass reactor mounted in a tubular oven. Experiments were carried out at 250° C. and normal pressure. The effluent gas was passed through a condenser and the condensate was collected and analysed by gas chromatography-mass spectrometry (GM-MS). The catalytic formation of n-hexyl GBL (n-hexyl γ-butyrolactone, $R_1=C_6H_{13}$, $R_2=H$) according to the equation

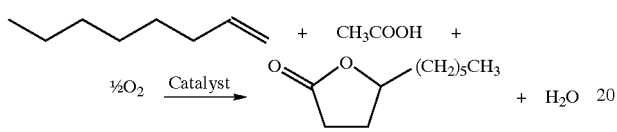

was demonstrated by running in a cyclic mode as follows:

$1^{st}$ cycle: The condensate was withdrawn after a period of time t1 (typically 20 minutes) and analysed. After a period of t2 minutes, the new condensate was sampled and analysed by GC-MS. The decrease in concentration of n-hexyl GBL from the first condensate to the second is due to the consumption of oxygen from the catalyst. This completes the first cycle.

The feed/nitrogen flow was stopped and the catalyst was then re-oxidised in a stream of air.

$2^{nd}$ cycle: The re-oxidised catalyst was set on stream again with the same flow as before. The condensate was again withdrawn after t3 minutes, the flow was continued for t4 minutes and then the experiment was stopped. The reappearance of product in the $2^{nd}$ cycle proves the catalytic nature of the reaction. The results for catalysts 1–3 are given in Table 1.

TABLE 1

Performances of Catalysts 1–3

| Catalyst | t1 (min) $1^{st}$ cycle | n-hex-GBL (arbitr.) | t2 (min) $1^{st}$ cycle | n-hex-GBL (arbitr.) | t3 (min) $2^{nd}$ cycle | n-hex-GBL (arbitr.) | t4 (min) $2^{nd}$ cycle | n-hex-GBL (arbitr.) |
|---|---|---|---|---|---|---|---|---|
| 1 | 20 | 3905 | 15 | 957 | 20 | 4294 | 10 | 0 |
| 2 | 20 | 2645 | 20 | 883 | 20 | 2791 | 15 | 420 |
| 3 | 20 | 1498 | 15 | 0 | 20 | 2009 | 20 | 652 |

Example 7

Formation of GBL from ethylene and acetic acid in the vapour phase.

An autoclave was charged with catalyst (2.0 g), pressurised with 5 bar feed gas and closed. The feed gas was either 20% ethylene in nitrogen or pure ethylene as stated in Table 2.

The autoclave was heated to 250° C. and at this temperature, acetic acid (AcOH) was injected through an injection loop by means of an overpressure of ethylene of 8 bar. After a period of 20 minutes, the autoclave was opened through a gas sample port connected to a 1 m 1/16" steel tube. The condensable parts were collected, diluted with diethyl ether to 2.0 ml and analysed by GC and GC-MS. The amount of product GBL for catalysts 1, 4 and 5 are given in Table 2.

TABLE 2

Performance of catalysts 1, 4 and 5

| Catalyst | AcOH (g) | % ethylene | GBL (mg/g AcOH) |
|---|---|---|---|
| 1 | 1 | 20 | 0.10 |
| 1 | 1 | 100 | 0.16 |
| 4 | 1 | 20 | 0.14 |
| 4 | 1 | 100 | 0.12 |
| 4 | 2 | 100 | 0.19 |
| 5 | 1 | 20 | 0.15 |
| 5 | 1 | 100 | 0.40 |

What is claimed is:

1. Process for the catalytic preparation of γ-butyrolactone having the general formula

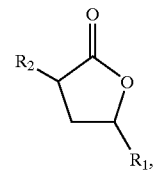

comprising:
reacting an olefin with the general formula $R_1CHCH_2$, with a carboxylic acid with the general formula $R_2CH_2COOH$, wherein $R_1$ and $R_2$ each represents a hydrogen, alkyl, cycloalkyl or aryl radical, and wherein the reaction is performed in the presence of oxygen in contact with a catalyst which comprises manganese, and wherein the catalyst is deposited on a support.

2. The process of claim 1, wherein the olefin and the carboxylic acid and the oxygen are reacted at a temperature of between 120° C. and 320° C.

3. The process as claimed in claim 2, wherein the carboxylic acid is acetic acid and the olefin is ethylene.

4. The process as claimed in claim 1, wherein the carboxylic acid is acetic acid and the olefin is ethylene.

5. Process for the catalytic preparation of γ-butyrolactone having the general formula

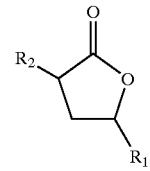

, comprising:
reacting an olefin with the general formula $R_1CHCH_2$, with a carboxylic acid with the general formula $R_2CH_2COOH$, wherein $R_1$ $R_2$ each represents a hydrogen, alkyl, cycloalkyl or aryl radical, and wherein the reaction is performed in the presence of oxygen in contact with a catalyst which comprises manganese, and wherein the catalyst is deposited on a support.

6. The process as claimed in claim 5, wherein the carboxylic acid is acetic acid and the olefin is ethylene.

7. The process of claim 5, wherein the olefin and the carboxylic acid and the oxygen are reacted at a temperature of between 120° C. and 320° C.

* * * * *